United States Patent [19]
Case

[11] Patent Number: 4,736,632
[45] Date of Patent: Apr. 12, 1988

[54] OPTICAL FIBRE SPLICING

[75] Inventor: Peter G. Case, Prescot, England

[73] Assignee: BICC Public Limited Company, London, England

[21] Appl. No.: 907,657

[22] Filed: Sep. 15, 1986

[30] Foreign Application Priority Data

Sep. 19, 1985 [GB] United Kingdom ............... 8523157

[51] Int. Cl.[4] .............................................. G01N 3/08
[52] U.S. Cl. ...................................... 73/827; 350/96.2
[58] Field of Search ........................ 73/827, 828, 830; 340/668; 65/4.1, 29; 350/96.2

[56] References Cited

U.S. PATENT DOCUMENTS 4,274,707  6/1981  Pacey et al. ...................... 350/96.20

FOREIGN PATENT DOCUMENTS 51807    3/1985  Japan ................................... 350/96.2
2039378  8/1980  United Kingdom .
2153548  8/1985  United Kingdom .

OTHER PUBLICATIONS

Vyas, M. K. R. et al, Tensile Testing Machine . . . Cables, Optics Communications, vol. 18, No. 4, Sep. '76, pp. 563–566.

*Primary Examiner*—Jerry W. Myracle
*Attorney, Agent, or Firm*—Anthony J. Casella; Gerald E. Hespos

[57] ABSTRACT

Optical fibre splice mechanical testing apparatus for use with optical fibre splicing equipment comprises two optical fibre clamping devices for mounting on splicing equipment at spaced positions spaced lengthwise of the two optical fibres to be spliced and located on opposite sides of the splicing station. One clamping device is constrained to move towards or away from the other clamping device in a direction lengthwise of the optical fibres between a first position nearer the splicing station and second position remote from the splicing station and is urged towards the second position by a coil spring. The movable clamping device can be temporarily maintained in the first position against the action of the coil spring. After a splice has been effected, the movable clamping device is temporarily maintained in the first position against the action of the coil spring, the clamping devices are clamped to the optical fibres, and movable clamping device is released so that it is urged by the coil spring towards the second position and a predetermined tensile force is applied to the splice. In its preferred form, the optical fibre splice mechanical testing apparatus is also employed to transfer the spliced optical fibres from the splicing station to a station at which a heat-shrinkable plastics sleeve can be applied to the splice, without any manhandling of the spliced optical fibres by an operator.

11 Claims, 3 Drawing Sheets

OPTICAL FIBRE SPLICING

This invention relates to end-to-end splicing of optical fibres. The invention is especially concerned with fusion splicing of optical fibres but it is to be understood that the invention is also applicable to splicing of fibres by means of an index matching adhesive.

It is an object of the present invention to provide simple and inexpensive apparatus for testing the mechanical strength of a splice between optical fibres immediately after the splice has been effected and before any form of protection has been applied to the splice.

According to the invention we provide, for use with optical fibre splicing equipment, optical fibre splice mechanical testing apparatus comprising two optical fibre clamping devices which are adapted to be permanently or detachably mounted on splicing equipment at positions spaced lengthwise of two optical fibres to be spliced and located on opposite sides of the splicing station, at least one of which clamping devices is constrained to move towards or away from the other clamping device in a direction lengthwise of said optical fibres between a first position nearer the the splicing station and a second position remote from the splicing station and is urged towards said second position by spring means and, associated with said movable clamping device, adjustable means for temporarily maintaining said movable clamping device in said first position against the action of said spring means, the arrangement being such that, after splicing of two optical fibres has been effected, the movable clamping device is temporarily maintained in said first position against the action of said spring means, the clamping devices are clamped to the optical fibres, and the adjustable means is released so that the movable clamping device is urged by said spring means towards said second position and a predetermined tensile force is applied to the splice between the optical fibres.

Generally, protection is applied to an optical fibre splice after the splice has been effected and, for this purpose, it has been the practice for an operator to remove spliced optical fibres from the splicing station and to place the splice in a station where such protection can be applied. In its preferred form, the optical fibre splice mechanical testing apparatus of the present invention can also be employed to transfer spliced optical fibres from the splicing station to a station at which protection can be applied to the splice, without any manhandling of the spliced optical fibres by an operator, thereby substantially reducing risk of any damage to the splice.

Accordingly, in the preferred form of optical fibre splice mechanical testing apparatus, the clamping devices are carried by a common support structure which can be so adjustably mounted on optical fibre splicing equipment that, after the splice between optical fibres clamped in the clamping devices has been mechanically tested and found satisfactory, the spliced optical fibres while still clamped by said clamping devices can be readily transferred to the splice protection-application station.

Preferably, the clamping devices are mounted at longitudinally spaced positions on a common shaft which extends lengthwise of and is transversely spaced from the splicing station and which is constrained to pivot about its longitudinal axis between a position in which spliced optical fibres in the splicing station are clamped in the clamping devices to a position in which said spliced optical fibres still clamped in the clamping devices are located in the splice protection-application station.

Each clamping device preferably comprises an elongate member which, at one of its ends, is mounted on the shaft and which, at the other of its ends, carries a pair of adjustable jaws between which an optical fibre can be clamped. Pivotable movement of the shaft on which the clamping devices are mounted is preferably effected by means of a system of levers and an associated adjustable stop by means of which the length of the arcuate path followed by the clamping devices when the shaft is pivoted can be readily adjusted.

The movable clamping device preferably is keyed to and slidably mounted on the shaft and the spring means urging the movable clamping device towards said second position preferably is a coil spring which extends between the movable clamping device and a stop which is secured to the shaft and through which the shaft extends.

The adjustable means for temporarily maintaining the movable clamping device in said first position against the action of the coil spring may take any convenient form but, in its simplest form, preferably comprises a sleeve which is slidably mounted on the shaft on the side of the movable clamping device remote from the coil spring and which is keyed to the shaft by means of bayonet-like fitting similar to that employed in sockets for the reception of electric light bulbs. In a more sophisticated arrangement, the sleeve may be in screw threaded engagement with the shaft so that, as the sleeve is unwound and the movable clamping device moves towards said second position under the action of the coil spring, a tensile force is gradually applied to the splice.

The optical fibre splice mechanical testing apparatus may include means for effecting all operations of the apparatus in sequence automatically.

The invention also includes optical fibre splicing equipment incorporating optical fibre splice mechanical testing apparatus as hereinbefore described.

The invention is further illustrated by a description, by way of example, of a preferred form of optical fibre splice mechanical testing apparatus, with reference to the accompanying drawings, in which.

Figure 1:
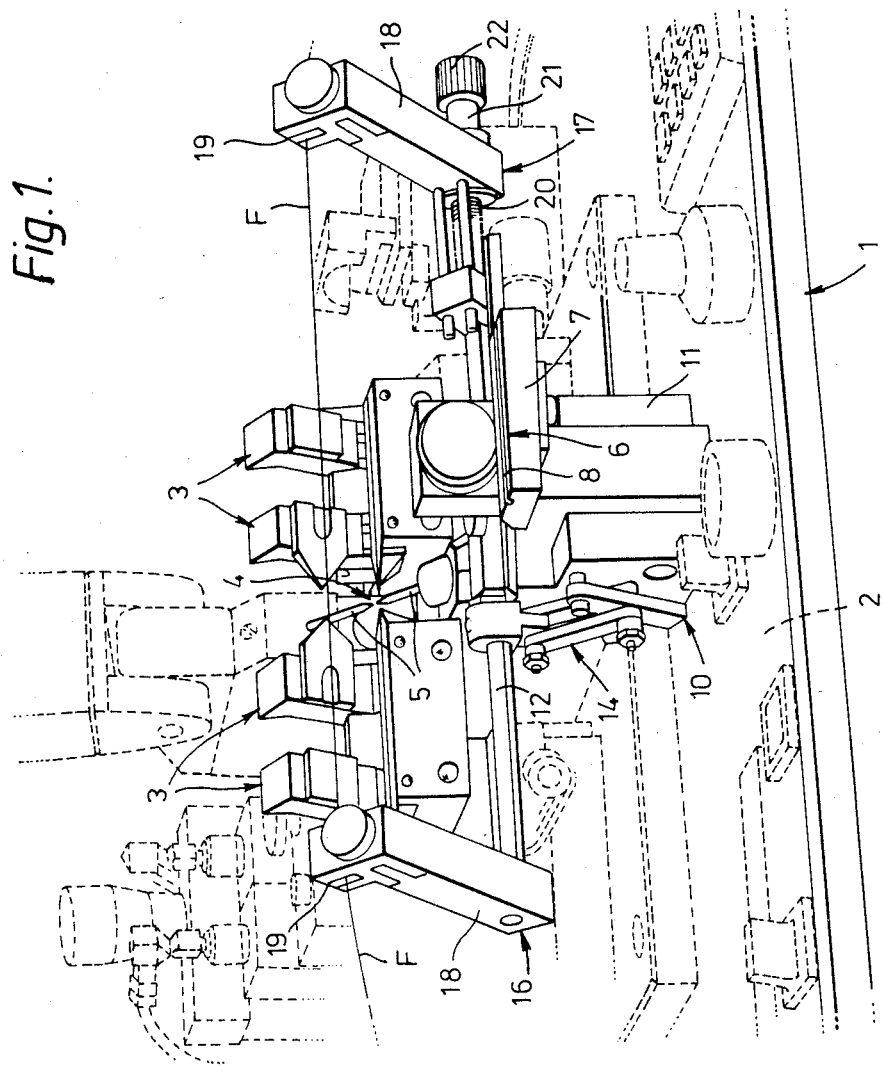
FIG. 1 is a fragmental pictorial view of optical fibre splicing equipment with the first preferred form of optical fibre splice mechanical testing apparatus mounted thereon.
Figure 2:
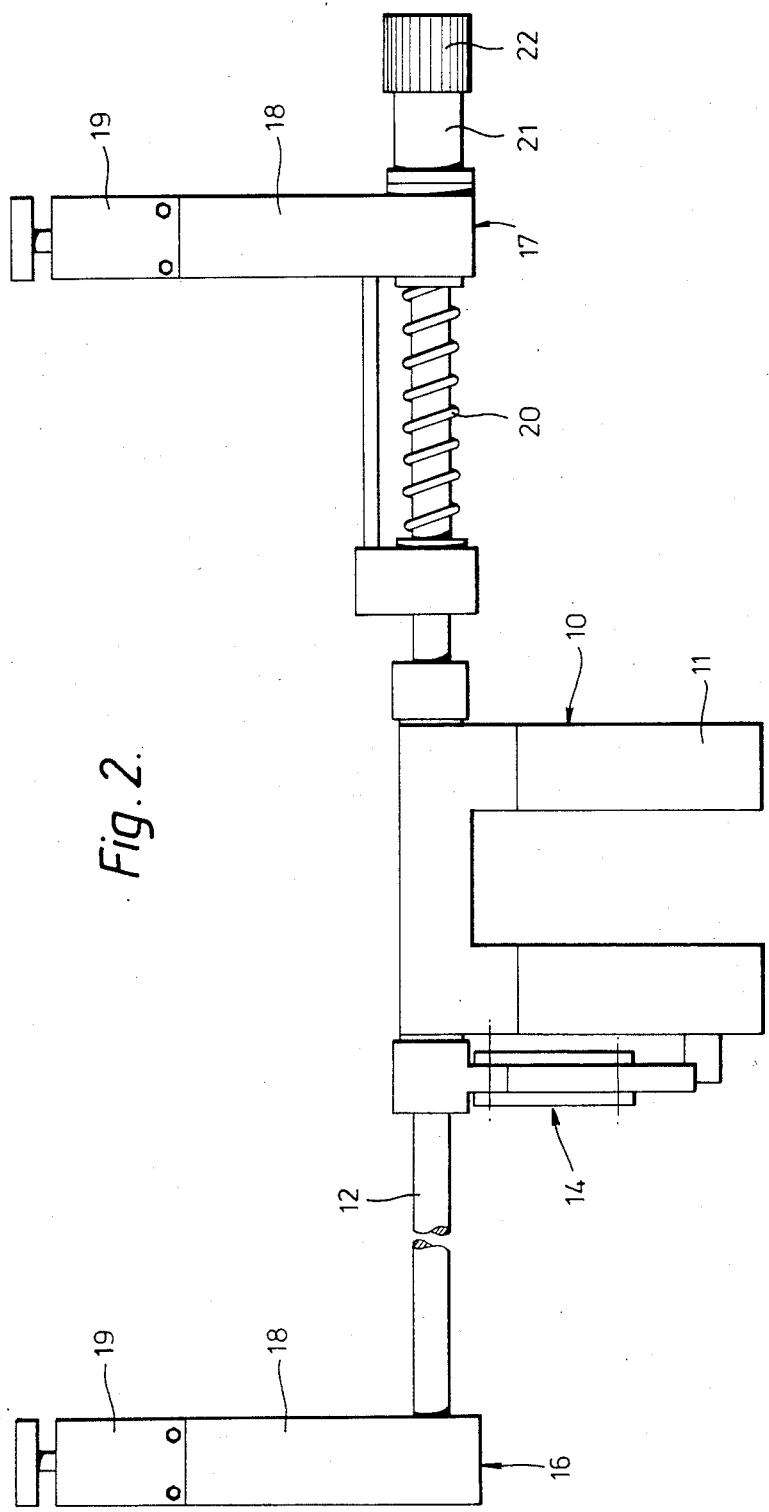
FIG. 2 is a side view of the preferred form of optical fibre splice mechanical testing apparatus.
Figure 3:
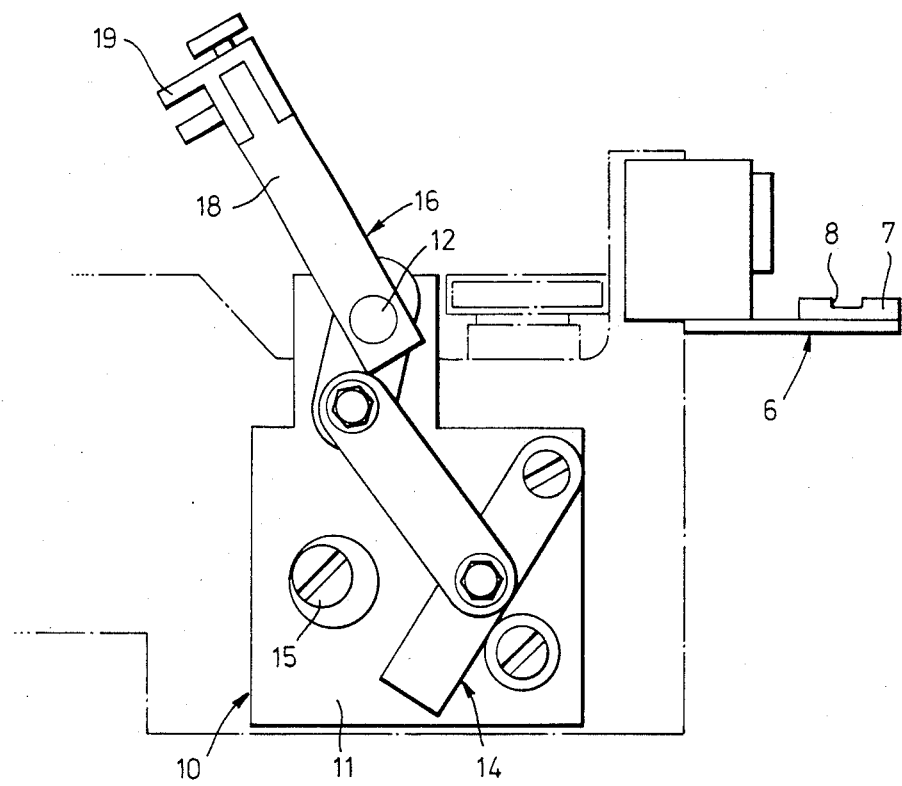
FIG. 3 is an end view of the preferred form of optical fibre splice mechanical testing apparatus.

Referring to FIGS. 1 to 3, optical fibre splicing equipment 1 includes a housing 2 on which optical fibre clamping assemblies 3 are positioned on opposite sides of a pair of electrodes 5 by means of which a fusion splice between two aligned optical fibres F can be effected and which constitute a splicing station 4. Also mounted on the housing 2 is a splice support table 7 in the upper surface of which is a splice support groove 8 and which constitutes a splice protection-application station 6 at which a heat-shrinkable plastics sleeve, positioned on a fusion splice between two aligned optical fibres, can be heated to cause it to shrink around the fusion splice.

Detachably mounted on the housing 2 of the optical fibre splicing equipment 1 is the preferred form of optical fibre splice mechanical testing apparatus 10. The apparatus 10 comprises a block 11, a shaft 12 which is mounted in the block and extends substantially parallel to optical fibres F to be spliced by the optical fibre splicing equipment 1 and which is pivotable about its longitudinal axis by means of a system 14 of levers, and an associated adjustable stop 15 by means of which the extent of pivotal movement of the shaft about its longitudinal axis can be readily adjusted. Mounted on the shaft 12 on opposite sides of the splicing station 4 are two optical fibre clamping devices 16 and 17, each of which comprises an elongate member 18 which, at one of its ends is mounted on the shaft and which, at the other of its ends, carries a pair of adjustable jaws 19 between which an optical fibre can be clamped. The adjustable jaws 19 are spring loaded sufficiently enough to grip an optical fibre F without causing any damage to any coating on the fibre.

The elongate member 18 of the clamping device 17 is constrained to move towards or away from the clamping device 16 in a direction lengthwise of the shaft 12 between a first position nearer the splicing station 4 and a second position remote from the splicing station and is urged towards the second position by a coil spring 20 which extends between the clamping device 17 and a stop 23 which is secured to the shaft and through which the shaft extends. Adjustable means for temporarily maintaining the movable clamping device 17 in the first position against the action of the coil spring 20 comprises a sleeve 21 which is slidably mounted on the shaft 12 on the side of the movable clamping device 17 remote from the coil spring 20 and which is keyed to the shaft by means of a bayonet-like fitting similar to that employed in sockets for the reception of electric light bulbs. Manipulation of the sleeve 21 can be effected by a knurled cap 22.

The adjustable stop 15 will be so adjusted that the shaft 12 is pivotable about its longitudinal axis from a first position in which spliced optical fibres in the splicing station 4 are clamped in the clamping devices 16, 17 to a second position in which said spliced optical fibres still clamped in the clamping devices are located in the splice protection-application station 6.

In use, a heat-shrinkable plastics sleeve (not shown) is slipped over one of two optical fibres F to be spliced, the optical fibres F are aligned in the clamping assemblies 3 of the optical fibre splicing equipment 1 with their end faces substantially abutting at the splicing station 4 and the fusion splice between the aligned optical fibres is effected. With the spring loaded jaws 19 of the clamping devices 16, 17 open and with the movable clamping device 17 urged to the first position nearer the splicing station 4 against the action of the coil spring 20 by means of the sleeve 21, the shaft 12 is caused to pivot about its longitudinal axis to the first position in which the spliced optical fibres F pass through the open jaws of the clamping devices, the heat-shrinkable plastics sleeve being positioned between the splice and one of the clamping devices. The spring loaded jaws 19 of the clamping devices 16, 17 are then actuated to cause the clamping devices to grip the spliced optical fibres.

The spliced optical fibres F are then released from the optical fibre clamping assemblies 3 of the splicing equipment 1 and the shaft 12 is pivoted about its longitudinal axis to withdraw the spliced optical fibres from the splicing station 4 to a position intermediate the splicing station and the splice protection-application station 6. The locking sleeve 21 is then released so that the movable clamping device 17 is urged in a direction away from the clamping device 16 by means of the coil spring 20 to impart a predetermined tensile force on the fusion splice between the optical fibres. If the fusion splice is found to be satisfactory, the heat-shrinkable plastics sleeve is slid over the fusion splice and further pivotal movement of the shaft 12 is effected to the second position in which the spliced optical fibres F still clamped in the clamping devices 16, 17, are located in the splice protection-application station 6. At this station, the heat-shrinkable sleeve is heated to cause it to shrink on to the fusion splice and when this has been completed the optical fibres are released from the jaws 19 of the clamping devices 16, 17.

What I claim as my invention is:

1. Optical fibre splice mechanical testing apparatus suitable for use with optical fibre splicing equipment incorporating a splicing station, which testing apparatus comprises two optical fibre clamping devices adapted to be mounted on said optical fibre splicing equipment at positions spaced lengthwise of two optical fibres to be spliced and located on opposite sides of the splicing station, at least one of said clamping devices being constrained to move towards or away from the other clamping device in a direction lengthwise of said optical fibres between a first position nearer the splicing station and a second position remote from the splicing station; spring means for urging said movable clamping device towards said second position; and, associated with said movable clamping device, adjustable means for temporarily maintaining said movable clamping device in said first position against the action of said spring means, the arrangement being such that, after splicing of two optical fibres has been effected, the movable clamping device is temporarily maintained in said first position by said adjustable means and against the action of said spring means, the clamping devices are clamped to the optical fibres, and the adjustable means is released so that the movable clamping device is urged by said spring means towards said second position and a predetermined tensile force is applied to the splice between the optical fibres.

2. Optical fibre splice mechanical testing apparatus as claimed in claim 1 suitable for use with optical fibre splicing equipment which also incorporates a splice protection —application station, wherein the clamping devices are carried by a common support structure which can be so adjustably mounted on said optical fibre splicing equipment that, after the splice between optical fibres clamped in the clamping devices has been mechanically tested and found satisfactory, the spliced optical fibres while still clamped by said clamping devices can be readily transferred to said splice protection-application station.

3. Optical fibre splice mechanical testing apparatus as claimed in claim 2, wherein the common support structure is a shaft on which the clamping devices are mounted at longitudinally spaced positions, said shaft extending lengthwise of and being transversely spaced from the splicing station and being constrained to pivot about its longitudinal axis between a position in which the spliced optical fibres in the splicing station are clamped in the clamping devices to a position in which said spliced optical fibres still clamped in the clamping devices are located in the splice protection-application station.

4. Optical fibre splice mechanical testing apparatus as claimed in claim 3, wherein each clamping device comprises an elongate member which, at one of its ends, is mounted on the shaft and which, at the other of its ends, carries a pair of adjustable jaws between which an optical fibre can be clamped.

5. Optical fibre splice mechanical testing apparatus as claimed in claim 3, wherein pivotal movement of the shaft on which the clamping devices are mounted is effected by means of a system of levers and an associated adjustable stop by means of which the length of the arcuate path followed by the clamping devices when the shaft is pivoted can be readily adjusted.

6. Optical fibre splice mechanical testing apparatus as claimed in claim 3, wherein the movable clamping device is keyed to and slidably mounted on the shaft.

7. Optical fibre splice mechanical testing apparatus as claimed in claim 3, wherein the spring means urging the movable clamping device towards said second position is a coil spring which extends between the movable clamping device and a stop which is secured to the shaft and through which the shaft extends.

8. Optical fibre splice mechanical testing apparatus as claimed in claim 7, wherein the adjustable means for temporarily maintaining the movable clamping device in said first position against the action of the coil spring comprises a sleeve which is slidably mounted on the shaft on the side of the movable clamping device remote from the coil spring and which is keyed to the shaft by means of a bayonet-like fitting.

9. Optical fibre splice mechanical testing apparatus as claimed in claim 7, wherein the adjustable means for temporarily maintaining the movable clamping device in said first position against the action of the coil spring comprises a sleeve which is in screw threaded engagement with the shaft on the side of the movable clamping device remote from the coil spring so that, as the sleeve is unwound and the movable clamping device moves towards said second position under the action of the coil spring, a tensile force is gradually applied to the splice.

10. Optical fibre splicing equipment including an optical fibre splicing station at which an end-to-end splice between two optical fibres can be effected, an optical fibre splice protection-application station at which protection can be applied to a spliced pair of optical fibres, and optical fibre splice mechanical testing apparatus as claimed in claim 2.

11. Optical fibre splicing equipment incorporating optical fibre splice mechanical testing apparatus as claimed in claim 1.

* * * * *